United States Patent [19]

Armitage et al.

[11] Patent Number: 4,501,727

[45] Date of Patent: Feb. 26, 1985

[54] THERAPEUTIC AGENT

[75] Inventors: Bernard J. Armitage; Margaret L. Donaldson, both of Nottingham, England

[73] Assignee: The Boots Company PLC, Nottingham, England

[21] Appl. No.: 446,721

[22] Filed: Dec. 3, 1982

[30] Foreign Application Priority Data

Dec. 8, 1981 [GB] United Kingdom ............... 8136989

[51] Int. Cl.³ .................... A61K 9/44; C07C 101/10
[52] U.S. Cl. ................................. 424/16; 260/501.16
[58] Field of Search ..................... 260/501.16; 424/16

[56] References Cited

U.S. PATENT DOCUMENTS

| | | | |
|---|---|---|---|
| 3,860,624 | 1/1975 | Diamond | 564/152 |
| 3,891,761 | 6/1975 | Sherlock | 424/266 |
| 3,903,134 | 9/1975 | Diamond | 260/501.16 |
| 3,932,499 | 1/1976 | Adams et al. | 260/501.16 |
| 3,985,788 | 10/1976 | Diamond | 260/501.16 |
| 3,987,197 | 10/1976 | Engel et al. | 260/501.16 |
| 4,209,638 | 6/1980 | Nicholson et al. | 562/401 |

FOREIGN PATENT DOCUMENTS

| | | |
|---|---|---|
| 887671 | 2/1981 | Belgium . |
| 892146 | 8/1982 | Belgium . |
| 0007116 | 1/1980 | European Pat. Off. . |
| 2158071 | 10/1972 | Fed. Rep. of Germany . |
| 3025448 | 1/1981 | Fed. Rep. of Germany . |
| 2106340 | 5/1972 | France . |
| 2413353 | 8/1979 | France . |
| 7014566 | 1/1982 | Japan . |
| 1105 | 2/1981 | South Africa . |

OTHER PUBLICATIONS

*Chemical Abstract,* vol. 98, #59892a, Antiinflammatory Formulations and Synthesis of Phenylacetate Derivatives, Ciba–Geigy.

Primary Examiner—Glennon H. Hollrah
Assistant Examiner—Raymond Covington
Attorney, Agent, or Firm—Gordon W. Hueschen

[57] ABSTRACT

The N-methyl-D-glucamine salt of (+)-2-(2-fluoro-4-biphenylyl)propionic acid, which is a novel compound with analgesic, anti-inflammatory and antipyretic properties and which is useful for treating inflammatory conditions including rheumatic disorders and as an analgesic. Pharmaceutical compositions containing the novel salt are also described. Also described are methods for preparing the novel salt by direct salification in an aqueous or non-aqueous medium, for example isopropanol, aqueous tetrahydrofuran, bis(methoxyethyl) ether and 4-methyl-1,3-dioxolan-2-one. Isopropanol is especially preferred.

8 Claims, No Drawings

THERAPEUTIC AGENT

This invention relates to a novel compound with therapeutic activity, to a process for preparing the novel compound and to therapeutic compositions containing it.

The compound 2-(2-fluoro-4-biphenylyl)propionic acid, known by the international non-proprietary name flurbiprofen, is a compound with anti-inflammatory, analgesic and antipyretic properties. It is a valuable therapeutic agent and is used, for example, in the treatment of rheumatoid arthritis, osteoarthritis and ankylosing spondylitis. Flurbiprofen exists as a racemic mixture of two optical isomers, the dextrorotatory or (+)-isomer and the laevorotatory or (−)-isomer. The present invention relates to the (+)-isomer of flurbiprofen, which is the pharmacologically active isomer.

The present invention provides the N-methyl-D-glucamine salt of (+)-2-(2-fluoro-4-biphenylyl)propionic acid, a novel compound which we have found to possess advantageous properties for use in therapy. For example, the salt has a high level of aqueous solubility and is useful for the preparation of aqueous solutions of (+)-2-(2-fluoro-4-biphenylyl)-propionic acid for parenteral injection.

The present invention provides pharmaceutical compositions which comprise the N-methyl-D-glucamine salt of (+)-2-(2-fluoro-4-biphenylyl)propionic acid, hereinafter termed the "novel salt", together with a pharmaceutically acceptable carrier. These compositions may take the form of any of the known compositions for enteral (i.e. oral or rectal), parenteral or topical use. The methods and excipients used in the preparation of such compositions are well-known in the art of pharmacy. The compositions may contain one or more additional active ingredients.

Compositions for oral administration are the known forms for such administration, for example tablets, capsules, granules and syrups. Tablets may be prepared by mixing the novel salt with an inert diluent such as lactose in the presence of a disintegrating agent, for example maize starch, and a lubricating agent, for example stearic acid, and tabletting the mixture by known methods. Similarly capsules, for example hard or soft gelatin capsules, containing the novel salt with or without added excipients, may be prepared in a conventional manner. Granules for reconstitution with water to provide a liquid preparation for oral administration may be prepared by mixing the novel salt with a water-soluble diluent, for example sucrose or lactose, and with a solution of a binding agent, for example polyvinylpyrrolidone, acacia or methylcellulose, and granulating the mixture by known methods. The granules are conveniently packaged in sachets, each sachet providing a unit dosage of the novel salt. Aqueous syrups containing the novel salt may be prepared in a conventional manner.

Compositions for rectal administration are the known pharmaceutical forms for such administration, for example suppositories with cocoa butter, polyethylene glycol or triglyceride bases.

Compositions for parenteral administration are the known pharmaceutical forms for such administration, for example sterile solutions in aqueous media.

Compositions for topical administration are the known pharmaceutical forms for such administration, for example ointments, creams, lotions and gels.

The compositions of the present invention may contain one or more conventional adjuvants such as sweetening agents, flavouring agents and colouring agents.

The compositions of the present invention in unit dosage form conveniently contain 10–250 mg., especially 25–100 mg. of the novel salt.

The novel salt of the present invention may be used in the treatment of rheumatic disorders and other inflammatory conditions in humans. Such rheumatic disorders include rheumatoid arthritis, osteoarthritis and ankylosing spondylitis. The novel salt is also useful as an analgesic, for example to provide pain relief in cases of headache, dental pain, post-episiotomy pain and pain associated with dysmenorrhoea.

The daily dosage of the novel salt for adults is generally within the range 10–500 mg., more usually 30–300 mg., given in single or divided doses.

The novel salt of the present invention may be prepared by direct salification of (+)-2-(2-fluoro-4-biphenylyl)propionic acid.

The salification may be carried out in an aqueous or non-aqueous liquid medium. For example, (+)-2-(2-fluoro-4-biphenylyl)propionic acid may be added portionwise to an aqueous solution of the stoichiometric amount of N-methyl-D-glucamine. Alternatively a solution of the acid in ethanol may be added to the aqueous solution of the stoichiometric amount of the amine. The solid salt may be isolated from the aqueous solution thereof by conventional means, for example evaporation to dryness.

The salification may be effected in a suitable hot organic solvent which is then cooled to cause crystallisation of the novel salt. Suitable solvents which may be used include, for example, isopropanol, tetrahydrofuran, bis(methoxyethyl) ether and 4-methyl-1,3-dioxolan-2-one. When tetrahydrofuran is used, it is preferred to include a small proportion, for example 2% $^v$/v, of water in the solvent at the salification stage in order to facilitate dissolution of the acid, and then remove the water by azeotropic distillation before crystallisation of the product. In this manner the novel salt is obtained in a very high yield and this method constitutes a preferred method of preparing the novel salt of the present invention.

Surprisingly, we have found that, when isopropanol is used as the solvent for salification and crystallisation, an almost quantitative yield of the novel salt is obtained, and the use of isopropanol is especially preferred.

We have found that, by means of the processes described above that involve a crystallisation of the product, the novel salt is obtained in a form that is more readily filterable than is the corresponding sodium salt when prepared by a similar process. This is a distinct advantage for the preparation of the novel salt of the invention on a commercial scale. In solid form the novel salt of the present invention is stable and non-hygroscopic and has the advantage of an improved stability to light compared with the parent acid (+)-2-(2-fluoro-4-biphenylyl)propionic acid.

The invention is illustrated by the following non-limitative examples, in which the term "active ingredient" designates the N-methyl-D-glucamine salt of (+)-2-(2-fluoro-4-biphenylyl)propionic acid and temperatures are given in degrees centigrade.

EXAMPLE 1

A mixture of (+)-2-(fluoro-4-biphenylyl)propionic acid (567 g., 2.32 mole), N-methyl-D-glucamine (453.5 g., 2.32 mole) and isopropanol (5250 ml.) was heated at 70°–80° to form a solution. The solution was clarified by filtration through a hot kieselguhr pad which was then washed with hot isopropanol (550 ml.). The combined filtrate and wash liquid was stirred and cooled to 0°–5° to give a crystalline product. The product was collected by filtration, washed with ice-cold isopropanol (500 ml.) and dried in vacuo at 50°. There was obtained the N-methyl-D-glucamine salt of (+)-2-(2-fluoro-4-biphenylyl)-propionic acid, m.p. 115.5°–118°. $[\alpha]_D^{21}$(C=1% $^w$/v in ethanol) $-21.6°$. The yield of salt obtained was 1006.8 g., which is 98.6% of the theoretical value.

EXAMPLE 2

A mixture of (+)-2-(2-fluoro-4-biphenylyl)propionic acid (2.44 g., 0.01 mole), N-methyl-D-glucamine (1.95 g., 0.01 mole), tetrahydrofuran (50 ml.) and water (1 ml.) was heated to form a solution. Water was removed from the mixture by azeotropic distillation, 22 ml. of distillate being collected which was replaced with 22 ml. of dry tetrahydrofuran. The resulting hot solution was clarified by filtration through a hot kieselguhr pad and then cooled with stirring to 5°. The resulting crystalline solid was collected by filtration, washed with ice-cold tetrahydrofuran (5.0 ml.) and dried in vacuo at 50°. There was obtained the N-methyl-D-glucamine salt of (+)-2-(2-fluoro-4-biphenylyl)propionic acid, m.p. 115.5°–118°, $[\alpha]_D^{21}$(C=1% $^w$/v in ethanol) $-21.6°$. The yield of product obtained was 4.19 g., which is 95.4% of the theoretical value.

EXAMPLE 3

Tablets are prepared from the following ingredients:

|  | Parts by Weight |
| --- | --- |
| Active Ingredient | 50.0 |
| Lactose | 78.5 |
| Polyvinylpyrrolidone | 5.0 |
| Maize Starch | 15.0 |
| Magnesium Stearate | 1.5 |

The active ingredient, the lactose and some of the starch are mixed and granulated with a solution of the polyvinylpyrrolidone in ethanol. The granulate is mixed with the magnesium stearate and the rest of the starch and the mixture is compressed in a tabletting machine to give tablets containing 50.0 mg. of the active ingredient.

EXAMPLE 4

Capsules are prepared in the following way. A mixture of the active ingredient (45 parts by weight) and lactose powder (205 parts by weight) is filled into hard gelatin capsules, each capsule containing 45 mg. of the active ingredient.

EXAMPLE 5

In the preparation of suppositories, 100 parts by weight of the finely ground active ingredient is incorporated in 1214 parts by weight of triglyceride suppository base and the mixture is formed into suppositories each containing 100 mg. of the active ingredient.

EXAMPLE 6

Vials containing a solution for injection are prepared from the following ingredients:

| Active Ingredient | 1100 g. |
| --- | --- |
| Mannitol | 1100 g. |
| Water | to 11 liters |

The active ingredient and mannitol are dissolved in some of the water and the volume of the solution is adjusted to 11 liters. The resulting solution is sterilised by filtration and filled into sterile vials each containing 1.65 ml. of solution.

I claim:

1. The N-methyl-D-glucamine salt of (+)-2-(2-fluoro-4-biphenylyl)propionic acid.

2. Pharmaceutical compositions which comprise the N-methyl-D-glucamine salt of (+)-2-(2- fluoro-4-biphenylyl)propionic acid together with a pharmaceutically acceptable carrier.

3. Pharmaceutical compositions as claimed in claim 2 in unit dosage form.

4. Pharmaceutical compositions as claimed in claim 3 in the form of tablets, capsules, granules, suppositories or parenteral injections.

5. A method for the alleviation of inflammation and/or pain in a human patient which comprises administering to the patient a therapeutically effective amount of the N-methyl-D-glucamine salt of (+)-2-(2-fluoro-4-biphenylyl)propionic acid.

6. A pharmaceutical composition of claim 2 in the form of granules.

7. A pharmaceutical composition of claim 3 in the form of capsules.

8. A method of claim 5 wherein the therapeutically-effective amount is administered in the form of a tablet, capsule, granule, suppository, or a parenteral injection.

* * * * *

UNITED STATES PATENT AND TRADEMARK OFFICE
CERTIFICATE OF CORRECTION

PATENT NO. : 4,501,727
DATED     : February 26, 1985
INVENTOR(S) : Bernard J. Armitage and Margaret L. Donaldson It is certified that error appears in the above—identified patent and that said Letters Patent is hereby corrected as shown below:

Title page, [56] (second column), References Cited, OTHER PUBLICATIONS, line 1, "Abstract," and "#59892a," should read -- Abstracts, -- and -- #59892u, --
(the original documents)

Signed and Sealed this

Twenty-seventh Day of August 1985

[SEAL]

Attest:

DONALD J. QUIGG

Attesting Officer     Acting Commissioner of Patents and Trademarks